United States Patent
Timari et al.

(10) Patent No.: US 7,964,731 B2
(45) Date of Patent: Jun. 21, 2011

(54) ISOTOPICALLY MARKED QUINOLINE DERIVATIVES AS ADENOSIN A3 RECEPTOR LIGANDS

(75) Inventors: Geza Timari, Vecses (HU); Kinga Boer, Pomaz (HU); Geza Toth, Szeged (HU); Csaba Tomboly, Szeged (HU)

(73) Assignee: Sanofi-Aventis, Paris (FR)

( * ) Notice: Subject to any disclaimer, the term of this patent is extended or adjusted under 35 U.S.C. 154(b) by 958 days.

(21) Appl. No.: 11/748,098

(22) Filed: May 14, 2007

(65) Prior Publication Data

US 2008/0027225 A1    Jan. 31, 2008

Related U.S. Application Data

(63) Continuation of application No. PCT/HU2005/000120, filed on Nov. 9, 2005.

(30) Foreign Application Priority Data

Nov. 15, 2004 (HU) .................................. 0402371

(51) Int. Cl.
*C07D 215/38* (2006.01)
(52) U.S. Cl. ........................ 546/162; 546/159
(58) Field of Classification Search .................. 546/159, 546/162
See application file for complete search history.

(56) References Cited

U.S. PATENT DOCUMENTS 6,969,723 B2 * 11/2005 Aranyi et al. .................. 514/313

OTHER PUBLICATIONS van Muijlwijk-Kozen, J Med Chem, vol. 41, pp. 3987-3993, 1998.*
Fozard, Br J Pharmacol, vol. 109, pp. 3-5, 1993.*
Baraldi, P., et al., Synthesis and Preliminary Biological Evaluation of [3H]-MRE 3008-F20: the First High Affinity Radioligand Antagonist for the Human A3 Adenosine Receptors, Bioorganic & Medicinal Chemistry Letters 10 (2000) 209-211.
Muller, C., et al., [3H]8-Ethyl-4-methyl-2-phenyl-(8R)-4,5,7,8-tetrahydro-1H-imidazo[2,1-i]-purin-5-one ([3H]PSB-11), a Novel High-Affinity Antagonist Radioligand for Human A3 Adenosine Receptors, Bioorganic & Medicinal Chemistry Letters 12 (2002) 501-503.
Van Galen P.J.M. et al., "A Binding Site Model and Structure-Activity Relationships for the Rat $A_3$ Adenosine Receptor", *Molecular Pharmacology* 45(6):1101-1111 (1994).
Olah M.E. et al., "1-4-Aminobenzyl-5'-N-Methylcarboxamidoadenosine, a High Affinity Radioligand for the Rat $A_3$ Adenosine Receptor", *Molecular Pharmacology* 45(5):978-982 (1994).
Stiles G.L. et al., "The $A_1$ Adenosine Receptor", *The Journal of Biological Chemistry* 260(19):10806-10811 (1985).

* cited by examiner

*Primary Examiner* — D. Margaret Seaman
(74) *Attorney, Agent, or Firm* — Scully, Scott, Murphy & Presser; Serena Farquharson-Torres

(57) ABSTRACT

The invention relates to adenozin $A_3$ receptor ligands labeled with iodine isotops of mass number 125, within those favorably to antagonists and their isomers, to the experimental materials containing them, to a process for the preparation of the compounds of the general formula (I)

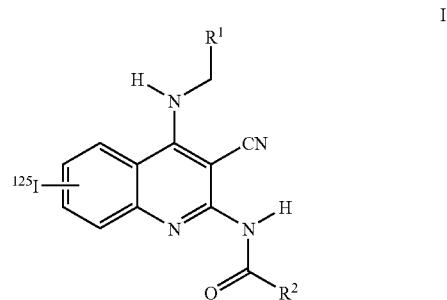

Figure 1:
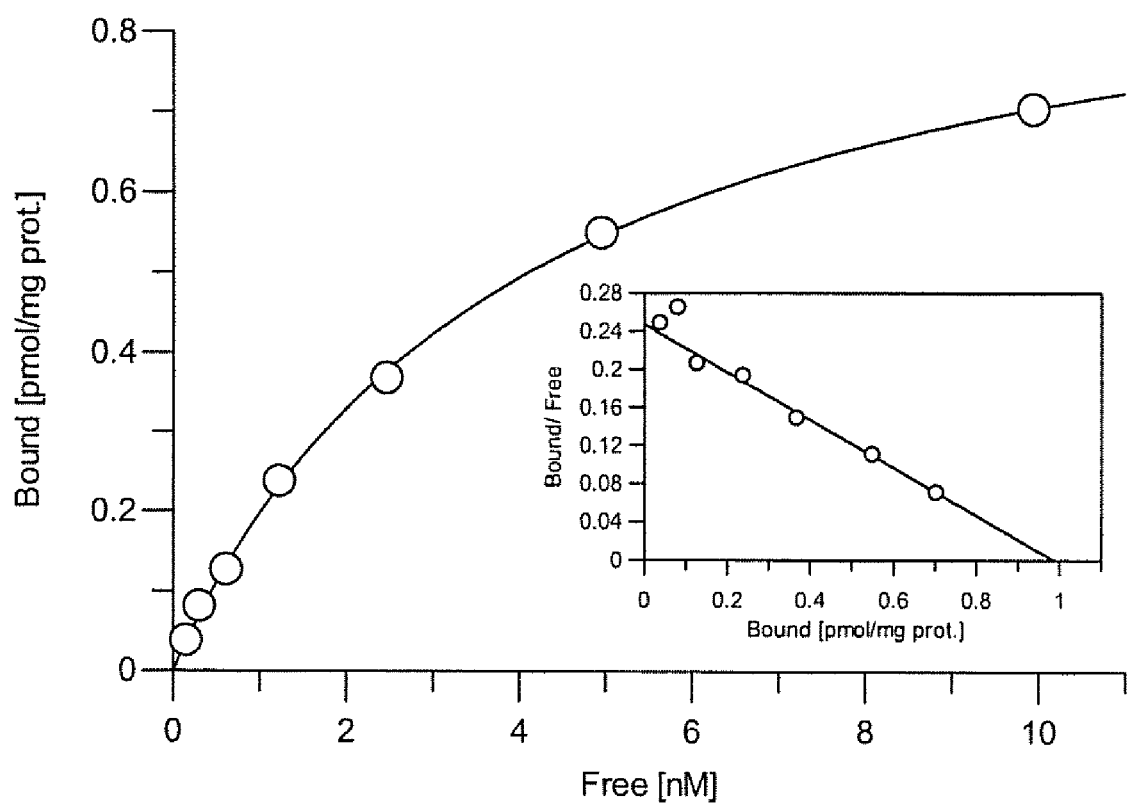

and their isomers, to the new intermediates of the general formula (II)

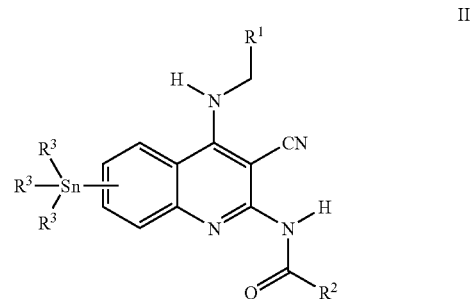

and to the preparation thereof.

21 Claims, 1 Drawing Sheet

ISOTOPICALLY MARKED QUINOLINE DERIVATIVES AS ADENOSIN A3 RECEPTOR LIGANDS

This application is a Continuation of International Application No. PCT/HU2005/000120, filed Nov. 9, 2005.

FIELD OF THE INVENTION

The present invention relates to adenozin $A_3$ receptor ligands labeled with iodine isotops of mass number 125, within those favourably to antagonists and their isomers, to the experimental materials containing them, to a process for the preparation of the compounds of the general formula (I)

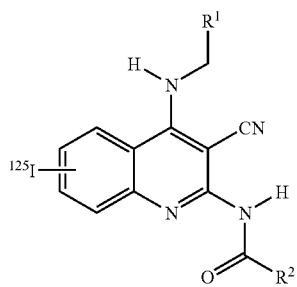

and their isomers, to the new intermediates of the general formula (II)

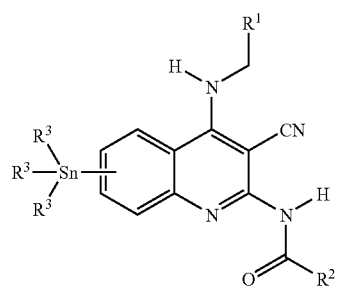

and to the preparation thereof.

BACKGROUND OF THE INVENTION

Adenosine is a well-known component of several endogenous molecules (ATP, $NAD^+$, nucleic acids). Besides, it plays an important regulatory role in many physiological processes. The effect of adenosine on heart function was discovered already in 1929. (Drury and Szentgyörgyi, J Physiol 68:213, 1929). The identification of an increasing number of physiological functions mediated by adenosine and the discovery of new adenosine receptor subtypes give possibilities for therapeutic application of specific ligands (Poulse, S. A. and Quinn, R. J. Bioorganic and Medicinal Chemistry 6:619, 1998).

To date, the receptors for adenosine have been classified into three main classes: $A_1$, $A_2$ and $A_3$. The $A_1$ subtype is partly responsible for inhibiting the adenylate cyclase by coupling to $G_i$ membrane protein, partly influences other second messenger systems. The $A_2$ receptor subtype can be subdivided into two further subtypes—$A_{2a}$ and $A_{2b}$—, which receptors stimulate the adenylate cyclase activity. The sequence of adenosine $A_3$ receptors have been recently identified from rat testis cDNA library. Later it was proved that it corresponds to a novel, functional adenosine receptor. The activation of the $A_3$ receptors is connected also with several second-messenger systems: inhibiting of adenylate cyclase, stimulating phospholipase C and D.

The adenosine receptors are found in several organs and regulate their functions. Both $A_1$ and $A_{2a}$ receptors play important roles in the central nervous system and cardiovascular system. In the CNS, the adenosine inhibits the release of synaptic transmitters which effect is mediated by $A_1$ receptors. In the heart, also the $A_1$ receptors mediate the negative inotropic, chronotropic and dromotropic effects of adenosine. The adenosine $A_{2a}$ receptors, which located relatively in a higher amount in the striatum, display a functional interaction with dopamine receptors in regulating the synaptic transmission. The $A_{2a}$ adenosine receptors on endothelial and smooth muscle cells are responsible for adenosine-induced vasodilation.

On the basis of mRNA identification, the $A_{2b}$ adenosine receptors are widely distributed in different tissues. They have been identified almost in every cell type, but its expression is the highest in the intestine and the bladder. This subtype probably also has important regulatory function in the regulation of the vascular tone and plays a role in the function of mast cells.

Contrary to $A_1$ and $A_{2a}$ receptors, where the tissue distribution was detected on the protein level, the presence of $A_{2b}$ and $A_3$ receptors was detected on the basis of their mRNA level. Expression levels for $A_3$ adenosine receptors are rather low comparing to other subtypes and highly species dependent. $A_3$ adenosine receptors are expressed primarily in the central nervous system, testis, immune system and appear to be involved in the modulation of mediator release from mast cells in immediate hypersensitivity reaction.

For therapeutic use it is essential to ensure that the molecule does not bind, or bind only in the case of very high concentration to the $A_1$, $A_{2a}$, and $A_{2b}$ sub-types of the adenosine receptor. Our present invention relates to the compounds of the general formula (I) labeled with iodo isotops of mass number 125, and to their salts, solvates and isomers, which have great selectivity for the $A_3$ sub-type of the adenosine receptor.

The [$^3$H]-MRE 3008-F20 adenosine $A_3$ receptor antagonist radioligand is known from the literature. (P. G. Baraldi, Bioorganic and Medicinal Chemistry Letters, 10, 209-211, 2000). Also known is the [$^3$H]PSB-11 $A_3$ receptor antagonist radioligand (C. H. Müller, Bioorganic and Medicinal Chemistry Letters, 12, 501-503, 2002).

Our aim was to prepare $A_3$ radioligands of antagonistic effect labelled with iodine isotop of mass number 125, since these have higher specific activity compared to those labelled with tritium. The goal was to prepare radioligands having strong affinity to the adenosin $A_3$ receptor, but at the same time showing high selectivity within the subtypes, i.e. binding in much higher concentration to the $A_1$, $A_{2a}$ and $A_{2b}$ receptors. A further aim was to have radioligands suitable for the characterisation of the $A_3$ receptor in the different tissues and for the study of the mechanism of action of $A_3$ antagonists.

SUMMARY OF THE INVENTION

The subject of our invention is compounds of the general formula (I)

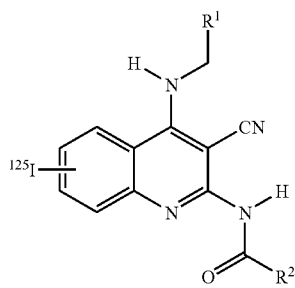

I and their isomers—where in the formula

R¹ stands for hydrogen atom or a straight or branched $C_{1-4}$ alkyl group, or a $C_{3-6}$ cycloalkyl group, or a phenyl group, thienyl group, or furyl group, optionally substituted with one or more straight or branched $C_{1-4}$ alkyl group, straight or branched $C_{1-4}$ alkoxy group, or halogen atom, or for a 5- or 6-membered heteroaromatic ring-containing one, two or three nitrogen atoms-, or for a 5-membered heteroaromatic ring-containing one nitrogen atom and one oxygen atom or one nitrogen atom and one sulphur atom—optionally substituted with one or more straight or branched $C_{1-4}$ alkyl group, straight or branched $C_{1-4}$ alkoxy group, or halogen atom;

R² stands for hydrogen atom or for a straight or branched $C_{1-4}$ alkyl group, or for a phenyl-, benzyl-, thienyl- or furyl-group-optionally substituted with a methylenedioxy group, or one or more straight or branched $C_{1-4}$ alkyl group, or straight or branched $C_{1-4}$ alkoxy-, hydroxyl-, trifluoromethyl- or cyano-group, or halogen atom-, or for a 5- or 6-membered heteroaromatic ring-containing one, two or three nitrogen atoms, or one nitrogen atom and one oxygen atom, or one nitrogen atom and one sulphur atom—optionally substituted with one or more straight or branched $C_{1-4}$ alkyl group, straight or branched $C_{1-4}$ alkoxy group, or halogen atom.

DETAILED DESCRIPTION OF THE INVENTION

Definition of the Terms

Detailed meanings of the above substituents are as follows:

By straight or branched $C_{1-4}$ alkyl group we mean methyl-, ethyl-, propyl-, isopropyl-, butyl-, isobutyl-, secondary-butyl-, tert.-butyl-, preferably ethyl- or methyl group.

By straight or branched $C_{1-4}$ alkoxy group we mean methoxy-, ethoxy-, propoxy-, isopropoxy-, butoxy-, isobutoxy-, sec.-butoxy-, tert.-butoxy-, preferably ethoxy- or methoxy group.

By $C_{3-6}$ cycloalkyl group we mean cyclopropyl-, cyclobutyl-, cyclopentyl- or cyclohexyl group.

The heteroaromatic ring containing one or two or three nitrogen atoms may mean pyrrole, imidazole, pyrazole, 1,2,3-triazole, 1,2,4-triazole, pyridine, pyrimidine, pyridazine, pyrazine and 1,3,4-triazine ring. The ring is optionally substituted with a $C_{1-4}$ alkyl, or alkoxy group or by a halogen atom.

The heteroaromatic ring containing one nitrogen atom and one oxygen or one sulphur atom means oxazole, isoxazole, thiazole, isothiazole ring. The ring is optionally substituted with a $C_{1-4}$ alkyl, or alkoxy group or by a halogen atom.

Particular Embodiments of the Invention

A favourable group of compounds of the general formula (I) is formed by the compounds—wherein R¹ stands for phenyl-, thienyl- or furyl group R² stands for 4-methoxyphenyl-, 3-methylphenyl-, 3-methoxyphenyl-, 2-thienyl-, 3-thienyl-, 2-furyl- or 3-furyl group.

Especially favourable are the following compounds complying with the above criteria:

4-Methoxy-N-(6-[$^{125}$I]iodo-4-benzylamino-3-cyano-quinolin-2-yl)benzamide

4-Methoxy-N-(6-[$^{125}$I]iodo-4-[2-thienylmethylamino]-3-cyanoquinolin-2-yl)benzamide Further subject of the invention is the preparation of the compounds of the general formula (I)

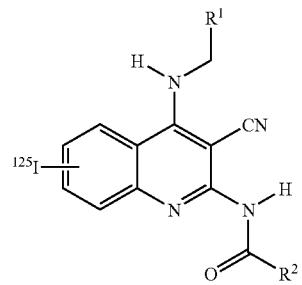

I and of the intermediates of the general formula (II).

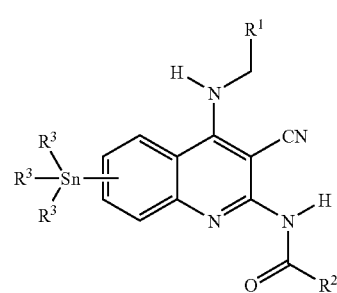

II

The intermediates of general formula (II) which are used in the preparation process according to the invention, are novel. In the general formula (II) substituents R¹ and R² have the meanings as defined above, R³ stands for straight or branched $C_{1-4}$ alkyl group, preferably methyl- or butyl group.

In the process according to our invention the compounds of the general formula (I) are prepared by reacting the appropriate compounds of the general formula (II) with unsupported [$^{125}$I]NaI, in the presence of an oxidant.

The reaction is carried out in aqueous methanolic medium (pH 3), at room temperature.

As oxidizing agents, peroxides for example hydrogen peroxide, N-halogeno-succinamides e.g. N-chloro-succinamide, or chlorosulphonamides, preferably chloramine-T can be used. The product is purified by reversed-phase high-performance liquid chromatographic (RP-HPLC) method using silica gel based $C_{18}$ modified packing as stationary phase and methanol-water binary mixture containing 0.1% (v/v) trifluoroacetic acid as eluent system, with flow rate of 0.9 ml/min. Detection is carried out by UV at 272 nm; detection of radioactivity is carried out by flow liquid scintillation method.

According to our invention the compound of general formula (II)

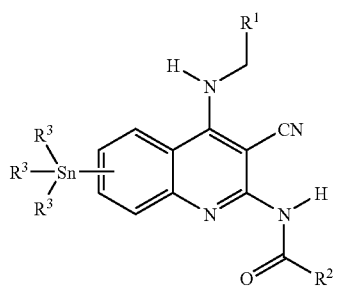

can be prepared from the appropriate quinoline of the general formula (III)

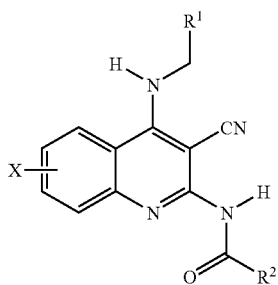

wherein $R^1$ and $R^2$ have the meanings as defined above and X stands for iodo- or bromo atom—by reacting it in the presence of palladium catalyst, organic or inorganic base and organic solvent, with a hexaalkyl-distannane compound. The product of general formula (II) is isolated. The exchange of the halogen atom for trialkyl-stannyl group is carried out in an organic solvent, for example in dioxane or dimethylformamide, or favourably in N-methyl-2-pyrrolidone. The reaction can be performed in a wide temperature range, preferably between 20° C.-100° C. As organic base trialkylamines, preferably triethylamine can be applied. For inorganic base alkali hydroxides, carbonates and acetates, preferably potassium acetate can be used. In the reaction palladium acetate, palladium chloride or tetrakis(triphenylphosphine)palladium(0) catalysts can be used (Z. P. Zhuang. M. P. Kung, C. Hou, D. M. Skovronsky, T. L. Gur, K. Plössl, J. Q. Trojanowski, V. M. Y. Lee, H. F. Kung, *J. Med. Chem.* 44, 1905, (2001)), but we have found that with tetrakis(tri(o-tolyl)phosphine)palladium (0) catalyst faster reaction and better yield is achieved.

The compounds of the general formula (III)

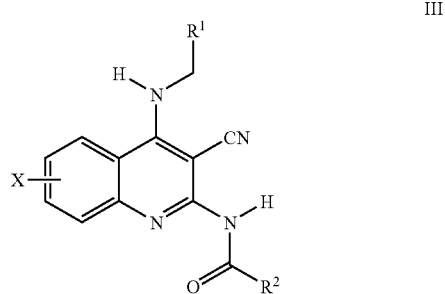

can be synthesized by the method described in patent application WO 02/096879.

The process according to our invention is shown in Reaction Scheme 1.

Further details of the invention are demonstrated in the Examples, without limiting the claims to the Examples.

EXAMPLES

Example 1

4-Methoxy-N-(6-[$^{125}$I]iodo4-benzylamino-3-cyano-quinolin-2-yl)benzamide

In the general formula (I) $R^1$ stands for phenyl group, $R^2$ stands for 4-methoxyphenyl group.

a.) To 8 µl of 0.1 mg/ml methanolic solution of 4-methoxy-N-(6-tributylstannyl-4-benzylamino-3-cyanoquinolin-2-yl)benzamide are added 25 µl (1.1 nmol) of 1% (v/v) methanolic solution of trifluoroacetic acid and 70 MBq [$^{125}$I]NaI solution (21 µl). To the reaction mixture 5 µl (2 nmol) of 0.1 mg/ml aqueous solution of chloramine-T is added and the mixture is stirred at room temperature for 15 minutes. After the incubation period the reaction is stopped by the addition of 7 µl (3.5 nmol) of 0.1 mg/ml sodium pyrosulfite solution and the product is immediately purified by using RP-HPLC method, applying UV and radioactivity detection. By this manner 31 MBq of the title compound is obtained (molar activity 81.4 GBq/mmol), radiochemical purity >95%. The purified product is stored in methanol-water (0.1% TFA) 3:1 mixture (activity concentration: 29 MBq/ml).

b.) 4-Methoxy-N-(6-tributylstannyl-4-benzylamino-3-cyanoquinolin-2-yl)benzamide.

0.33 g of 4-methoxy-N-(6-iodo-4-benzylamino-3-cyanoquinolin-2-yl)benzamide is dissolved in 5 ml of N-methyl-2-pyrrolidone and to the solution 240 mg of potassium acetate, 50 mg of tetrakis(tri(o-tolyl)phosphine)palladium(0) and 0.6 ml of hexabutyl distannane are added. The reaction mixture is stirred at room temperature under argon atmosphere for 16 hours, then it is poured onto 20 ml of water and extracted with 2×20 ml of toluene. The united toluene phase is dried over sodium sulfate, filtered and evaporated under reduced pressure. The residue is chromatographed on a silicagel coloumn using chloroform-ethyl acetate (10:0.5) mixture as eluent. After evaporation of the pure fractions 250 mg of the title compound is obtained.

$^1$H-NMR (CDCl$_3$) δ 0.9 (m, 9H), 1.1 (M, 6H), 1.3 (m, 6H), 1.55 (m, 6H), 3.8 (s, 3H), 5.08 (d, 2H), 7.06 (d, 2H), 7.2-7.4 (m, 5H), 7.55 (d, 2H), 7.9-8.1 (m, 3H), 8.66 (m, 1H), 10.7 (s, 1H).

Example 2

4-Methoxy-N-(6-[$^{125}$I]iodo-4-[2-thienylmethylamino]-3-cyanoquinolin-2-yl)benzamide In the general formula (I) $R^1$ stands for thienyl group, $R^2$ stands for 4-methoxyphenyl group.

a.) To 8 µl (1.1 nmol) of 0.1 mg/ml methanolic solution of 4-methoxy-N-(6-tributylstannyl-4-[2-thienylmethylamino]-3-cyanoquinolin-2-yl)benzamide are added 25 µl (1.1 nmol) of 1% (v/v) methanolic solution of trifluoroacetic acid and 70 MBq [$^{125}$I]NaI solution (21 µl). To the reaction mixture 5 µl (2 nmol) of 0.1 mg/ml aqueous solution of chloramine-T is added and the mixture is stirred at room temperature for 15 minutes. After the incubation period the reaction is stopped by the addition of 7 µl (3.5 nmol) of 0.1 mg/ml sodium pyrosulfite solution and the product is immediately purified by RP-HPLC method, while applying UV and radioactivity detection. By this manner 28 MBq of the title compound is obtained (molar activity 81.4 GBq/mmol), radiochemical purity >95%. The purified product is stored in methanol-water (0.1% TFA) 3:1 solvent mixture (activity concentration: 28 MBq/ml).

b.) 4-Methoxy-N-(6-tributylstannyl-4-[2-thienylmethylamino]-3-cyanoquinolin-2-yl)benzamide.

0.3 g 4-Methoxy-N-(6-iodo-4-[2-thienylmethylamino]-3-cyanoquinolin-2-yl)benzamide is dissolved in 5 ml of N-methyl-2-pyrrolidone and to the solution 240 mg of potassium acetate, 50 mg of tetrakis(tri(o-tolyl)phosphine)palladium(0) and 0.6 ml of hexabutyl distannane are added. The reaction mixture is stirred at room temperature under argon atmosphere for 16 hours, then it is poured onto 20 ml of water and extracted with 2×20 ml of toluene. The united toluene phase is dried over sodium sulfate, filtered and evaporated under reduced pressure. The residue is chromatographed on a silicagel coloumn using chloroform-ethyl acetate (10:0.5) mixture as eluent. By evaporating the pure fractions 235 mg of the title compound is obtained.

$^1$H-NMR (CDCl$_3$) δ 0.9 (m, 9H), 1.1 (M, 6H), 1.3 (m, 6H), 1.55 (m, 6H), 3.85 (s, 3H), 5.1 (d, 2H), 6.9-7.17 (m, 4H), 7.43-7.54 (m, 2H), 8.03 (m, 3H), 8.72-8.82 (m, 2H), 10.86 (s, 1H).

Example 3

A./ Biological Methods

Human Adenozin $A_1$ Receptor Binding

Preparing membrane suspension: collect ovarium cells of cloned Chinese hamster expressing human $A_1$ receptors (further: CHO-h$A_1$), wash them three times with PBS, centrifuge (1000×g 10 min.) and homogenize (B.Braun Potter S) at 1500/min rotation speed. Buffer: 50 mM Tris HCl, pH 7,4. Centrifuge this homogenized mixture (43.000 g, 10 min), suspense the pellet in the above buffer with adjustment of the protein concentration to 5 mg/mL (Bradford method) and complete with 2 U/mL ADA.

Binding protocol: incubate CHO-h$A_1$ membrane preparation (50 µg protein content), in the presence of the test compound and 10 nM [$^3$H]CCPA (2-chloro-$N^6$-cyclopenthyl-adenosine) (80.000 dpm) in incubation buffer (50 mM Tris HCl, pH 7.4, 2 U/mL adenosine deaminase). The non-specific binding is defined in the presence of 10 µM R-PIA ($N^6$-[L-2-phenylisopropyl]adenosine) in a total volume of 100 µL for 3 hr at room temperature. Filter over Whatman GF/B glass fibre filters (presoaked in 0.5% polyethylimine for 3 hours), wash 4× with 1 mL ice-cold 50 mM Tris HCl (pH 7.4) on 96-well Brandel Cell Harvester. Detection of activity: in 96-well plate in the presence of HiSafe-3 cocktail in beta-counter (1450 Microbeta, Wallac). Inhibition [%]=100−((activity in the presence of test compound−non-specific activity)/(total activity−non-specific activity))*100

Human Adenosine $A_{2a}$ Receptor Binding

Incubate 7 µg of membranes (human $A_2$ adenosine receptors transfected into HEK-293 cells, source: Receptor Biology, Inc.), in the presence of the test compound and 20 nM [$^3$H]CGS-21680 (2-[p-(2-carbonylethyl)phenylethylamino]-5'-N-ethylcarboxamido-adenosine) (200.000 dpm) in incubation buffer (50 mM Tris HCl, 10 mM MgCl$_2$, 1 mM EDTA, 2 U/mL adenosine deaminase, pH 7.4). The non-specific binding is defined in the presence of 100 µg NECA (5'-N-ethylcarboxamido-adenosine) in a total volume of 100 µl for 90 min at room temperature. Filter in vacuum over Whatman GF/B glass fibre filters (presoaked for 3 hours in 0.5% polyethylimine), wash 4× with 1 mL ice-cold buffer (50 mM Tris HCl, 10 mM MgCl$_2$, 1 mM EDTA, 0.9% NaCl, pH 7.4) on 96-well Brandel Cell Harvester. Detection of activity: in beta-counter (1450 Microbeta, Wallac) in the presence of 200 µL HiSafe-3 cocktail. Inhibition [%]=100−((activity in the presence of test compound−non-specific activity)/(total activity−non-specific activity))*100.

Human Adenosine $A_{2b}$ Receptor Binding

Binding protocol: incubate 20.8 µg of membranes (human $A_{2b}$ adenosine receptors transfected into HEK-293 cells, source: Receptor Biology, Inc.), in the presence of the test compound and 32.4 nM [$^3$H]DPCPX (8-cyclopenthyl-1,3-dipropylxanthine) (800.000 dpm) in incubation buffer (50 mM Tris-HCl, 10 mM MgCl$_2$, 1 mM EDTA, 0.1 mM benzamidine, 2 U/mL adenosine deaminase, pH 6.5). The non-specific binding is defined in the presence of 100 µM NECA (5'-N-ethylcarboxamido-adenosine) in a total volume of 100 µL for 30 min at room temperature. Filter under 25 Hgmm vacuum over Whatman GF/C glass fibre filters (presoaked in 0.5% polyethylimine for 3 hours), wash 4× with 1 mL ice-cold 50 mM Tris HCl (pH 6.5) on 96-well Brandel Cell Harvester. Detection of activity: in beta-counter (1450 Microbeta, Wallac) in the presence of 200 µL of HiSafe-3 cocktail. Inhibition [%]=100−((activity in the presence of test compound−non-specific activity)/(total activity−non-specific activity))*100

Human Adenosine A$_3$ Receptor Binding

Preparing membrane suspension: collect ovarium cells of cloned Chinese hamster expressing human A$_3$ receptors (further: CHO-hA$_3$), wash them three times with PBS, centrifuge (1000×g 10 min.) and homogenize (B.Braun Potter S) at 1500/min rotation speed. Buffer: 50 mM Tris, 10 mM MgCl$_2$, 1 mM EDTA, pH 8.0. Centrifuge this homogenized mixture (43.000 g, 10 min), suspense the pellet in the above buffer with adjustment of the protein concentration to 0.1 mg/mL (Bradford method) and complete with 2 U/mL ADA.

Receptor Binding in the Presence of [$^{125}$I]AB-MECA:

Incubate the CHO-hA$_3$ membrane preparation (protein content 2 µg) in the presence of the test compound and 0.5 nM [$^{125}$I]AB-MECA (4-amino-3-iodo-benzyl-5'-N-methylcarboxamide-adenosine) (100.000 cpm) in incubation buffer (50 mM Tris, 10 mM MgCl$_2$, 1 mM EDTA, 2 U/mL adenosine deaminase, pH 8.0). The non-specific radioligand binding is defined in the presence of 100 µM R-PIA (N$^6$-[L-2-phenylisopropyl]adenosine) in a total volume of 50 µL for 60 min at room temperature. Filter under 25 Hgmm vacuum over Whatman GF/C glass fibre filters (presoaked in 0.5% polyethylimine for 3 hours), wash 4× with 1 mL ice-cold buffer (50 mM Tris, 10 mM MgCl$_2$, 1 mM EDTA, pH 8) on 96-well Brandel Cell Harvester. Detection of radioactivity: in gamma-counter (1470 Wizard, Wallac). Inhibition [%]=100−((activity in the presence of test compound−non-specific activity)/(total activity−non-specific activity))*100.

Receptor Binding in the Presence of the Radioactive Iodine-Containing Compound of Example 2/a:

Incubate the CHO-hA$_3$ membrane preparation (protein content 4 µg) in the presence of the test compound and 0.5 nM of the compound containing radioactive iodine (100.000 cpm), described in Example 2/a, in incubation buffer (50 mM Tris, pH 8.0, 10 mM MgCl$_2$, 1 mM EDTA, 0.08% CHAPS, 0.5% BSA, 2 U/mL adenosine deaminase). The non-specific radioligand binding is defined in the presence of 100 µM R-PIA (N$^6$-[L-2-phenylisopropyl]adenosine) in a total volume of 50 µL for 60 min at room temperature. Keep the isotop preparation and the reaction mixture in polyethylene tube to decrease adsorption. Filter under 25 Hgmm vacuum over Whatman GF/C glass fibre filters (presoaked in 0.5% polyethylimine for 3 hours), wash 4× with 1 mL ice-cold buffer (50 mM Tris (pH 8), 10 mM MgCl$_2$, 1 mM EDTA, 0.08% CHAPS, 0.25% BSA) on 96-well Brandel Cell Harvester. Detection of radioactivity: in gamma-counter (1470 Wizard, Wallac). Inhibition [%]=100−((activity in the presence of test compound−non-specific activity)/(total activity−non-specific activity))*100.

B./ Biological Results

I Affinity of the Un-Labeled Iodine-Containing Compound Given in Example 2/b as Starting Material (i.e. the Un-Labeled Analogue of the New Radioligand Given in Example 2/a) to the Adenosine Receptor Sub-Types in the Presence of Known Radioligands The affinity of the starting compound of Example 2/b to the adenosine A$_3$ receptor (K$_i$=1.5 nM) exhibits at least thousand-fold selectivity compared to the other adenosine receptor sub-types (Table 1).

TABLE 1

Characterisation of the starting compound of Example 2/b as regards its affinity to the adenosine receptors

| | hA$_3$ | Inhibition in 1 µM | | |
|---|---|---|---|---|
| | [$^{125}$I]AB-MECA | hA$_1$ [$^3$H]CCPA | hA$_{2A}$ [$^3$H]CGS21680 | hA$_{2B}$ [$^3$H]DPCPX |
| The starting compound of Example 2/b | K$_i$ = 1.5 nM | 4% | 29% | −16% |

II/A Investigation of the New Radioactive Iodine-Containing Compound of Example 2/a on the Human Adenosine A$_3$ Receptor by Scatchard Analysis Used for the Characterisation of Radioligands On the basis of radioisotop saturation curves, by Scatchard analysis (G. Scatchard, Ann. N. Y. Acad. Sci. 51:660, 1949) the dissociation constant (K$_D$) of the new radioligand of Example 2/a on CHO-hA$_3$ membrane preparation is determined. In the investigated concentration range (0.156 nM-10 nM) the radioligand binds to only one binding place in the presence of a membrane preparate containing 4 µg of protein. The value of K$_D$ was found to be 4 nM, the maximal binding capacity 985 femtomol/1 mg protein (see FIG. 1).

FIG. 1: Scatchard saturation curve of the new radioligand of Example 2/a in the presence of CHO-hA$_3$ membrane preparation II/B Comparison of a Known Adenosine A$_3$ Radioligand with the New Radioligand of Example 2/a on the Basis of the Affinity Values of Reference compounds, in the Presence of 4 µg CHO-hA$_3$ Preparate Knowing the K$_D$ values, by the Cheng-Prusoff equation (Y. J. Cheng and W. H. Prusoff, Biochem. Pharmacol. 22:3099, 1973) the K$_i$ constants of the investigated reference compounds and that of the starting compound of Example 2/b (i.e. of the un-labeled analogue of the new radioligand of Example 2/a) were calculated on the basis of the IC$_{50}$ values. The reference compounds exhibited similar affinity values in the presence of the known and of the new radioligands, proving the suitability of the radioligand of Example 2/a. The un-labeled analogue of the new radioligand exhibited a K$_i$ value nearly equal to the K$_D$ value of the isotop-labeled form (4.0 nM and 1.3 nM), also proving the specific binding of the new radioligand (see Table 2).

TABLE 2

Comparison of a known adenosine A$_3$ radioligand and the new radioligand of Example 2/a with the help of affinity values of reference compounds, in the presence of 4 µg CHO-hA$_3$ preparation.

| | [$^{125}$I]AB-MECA | The radioligand given in Example 2/a |
|---|---|---|
| | K$_i$ | |
| R-PIA | 65 nM | 150 nM |
| Cl-IB-MECA | 3.3 nM | 5.9 nM |
| The starting compound of Example 2/b | 1.5 nM | 1.3 nM |

We claim:

1. A compound of formula (I)

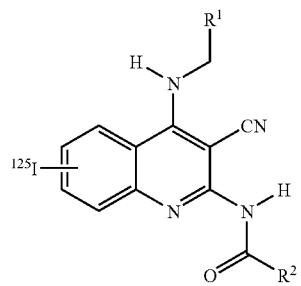

wherein

R[1] is hydrogen, a straight or branched $C_{1-4}$ alkyl group, a $C_{3-6}$ cycloalkyl group, a phenyl group, thienyl group, or furyl group, each of which is optionally substituted with one or more straight or branched $C_{1-4}$ alkyl group, straight or branched $C_{1-4}$ alkoxy group, or halogen atom, or a 5- or 6 membered heteroaromatic ring containing one, two or three nitrogen atoms, or a 5-membered heteroaromatic ring containing one nitrogen atom and one oxygen atom or one nitrogen atom and one sulphur atom, each of which is optionally substituted with one or more straight or branched $C_{1-4}$ alkyl group, straight or branched $C_{1-4}$ alkoxy group, or halogen atom; and R[2] is hydrogen, a straight or branched $C_{1-4}$ alkyl group, or a phenyl, benzyl, thienyl or furyl group, each of which is optionally substituted with a methylenedioxy group, one or more straight or branched $C_{1-4}$ alkyl group, straight or branched $C_{1-4}$ alkoxy, hydroxy, trifluoromethyl, cyano, or halogen atom, or a 5- or 6-membered heteroaromatic ring containing one, two or three nitrogen atoms, or one nitrogen atom and one oxygen atom, or one nitrogen atom and one sulphur atom, each of which is optionally substituted with one or more straight or branched $C_{1-4}$ alkyl group, straight or branched $C_{1-4}$ alkoxy group, or halogen atom;

or an isomer thereof.

2. The compound according to claim 1, wherein:

R[1] is phenyl, thienyl or furyl group;

R[2] is 4-methoxyphenyl, 3-methylphenyl, 3-methoxyphenyl, 2-thienyl, 3-thienyl, 2-furyl or 3-furyl group;

or an isomer thereof.

3. The compound according to claim 1, which is

4-Methoxy-N-(6-[$^{125}$I]iodo-4-benzylamino-3-cyano-quinolin-2-yl)benzamide, or 4-Methoxy-N-(6-[$^{125}$I]iodo-4-[2-thienylmethylamino]-3-cyanoquinolin-2-yl)benzamide.

4. A process for preparing the compound of formula (I) according to claim 1, comprising reacting a trialkyl-stannyl compound of formula (II)

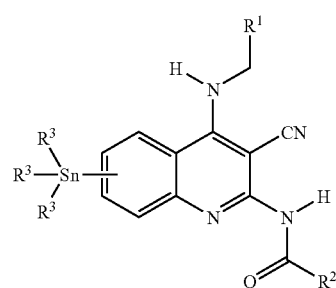

where R[1] and R[2] are as defined in claim 1, and R[3] is straight or branched $C_{1-4}$ alkyl group, with [$^{125}$I]NaI, in the presence of an oxidant.

5. The process according to claim 4, wherein the oxidant is peroxide, halogeno-succinamide, or chlorosulfonamide.

6. The process according to claim 4, wherein the oxidant is hydrogen peroxide, N-chloro-succinamide, or chloramin-T.

7. The process according to claim 4, wherein [$^{125}$I]NaI is un-supported [$^{125}$I]NaI.

8. The process according to claim 4, wherein the reaction is carried out in aqueous-methanolic medium having pH about 3, and at room temperature.

9. The process according to claim 4, wherein the compound of formula (I) is isolated by RP-HPLC method.

10. The process according to claim 9, wherein the isolation by RP-HPLC method is carried out by using silica gel based $C_{18}$ modified packing as stationary phase, using methanol-water binary eluent system containing 0.1% (v/v) trifluoroacetic acid with flow-rate of 0.9 mL/min, and under UV detection and on-line radioactivity detection.

11. A compound of formula (II)

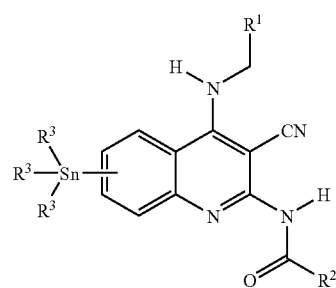

wherein

R[1] is hydrogen, a straight or branched $C_{1-4}$ alkyl group, a $C_{3-6}$ cycloalkyl group, a phenyl group, thienyl group, or furyl group, each of which is optionally substituted with one or more straight or branched $C_{1-4}$ alkyl group, straight or branched $C_{1-4}$ alkoxy group, or halogen atom, or a 5- or 6 membered heteroaromatic ring containing one, two or three nitrogen atoms, or a 5-membered heteroaromatic ring containing one nitrogen atom and one oxygen atom or one nitrogen atom and one sulphur atom, each of which is optionally substituted with one or more straight or branched $C_{1-4}$ alkyl group, straight or branched $C_{1-4}$ alkoxy group, or halogen atom;

$R^2$ is hydrogen, a straight or branched $C_{1-4}$ alkyl group, or
a phenyl, benzyl, thienyl or furyl group, each of which is optionally substituted with a methylenedioxy group, one or more straight or branched $C_{1-4}$ alkyl group, straight or branched $C_{1-4}$ alkoxy, hydroxy, trifluoromethyl, cyano, or halogen atom, or
a 5- or 6-membered heteroaromatic ring containing one, two or three nitrogen atoms, or one nitrogen atom and one oxygen atom, or one nitrogen atom and one sulphur atom, each of which is optionally substituted with one or more straight or branched $C_{1-4}$ alkyl group, straight or branched $C_{1-4}$ alkoxy group, or halogen atom; and $R^3$ is straight or branched $C_{1-4}$ alkyl group;
or an isomer thereof.

12. The compound according to claim 11, wherein:
$R^1$ and $R^2$ are each independently phenyl or thienyl group; and
$R^3$ is methyl or butyl group;
or an isomer thereof.

13. A process for preparing the compound of formula (II) according to claim 11, comprising reacting a compound of the general formula (III)

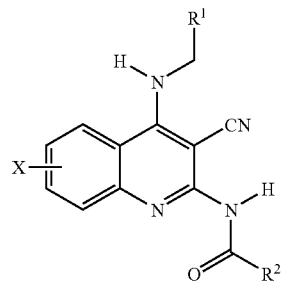

where X is iodo or bromo, $R^1$ and $R^2$ are as defined in claim 11, with hexaalkyl distannane, in an organic solvent and in the presence of a base and a palladium catalyst.

14. The process according to claim 13, wherein the organic solvent is dioxane, dimethyl formamide, or N-methyl-2-pyrrolidone.

15. The process according to claim 13, wherein the base is an organic base or an inorganic base.

16. The process according to claim 15, wherein the organic base is trialkylamine.

17. The process according to claim 16, wherein the trialkylamine is triethylamine.

18. The process according to claim 15, wherein the inorganic base is alkali hydroxide, alkali carbonate or alkali acetate.

19. The process according to claim 18, wherein the alkali acetate is potassium acetate.

20. The process according to claim 13, wherein the palladium catalyst is palladium acetate, palladium chloride, tetrakis(triphenylphosphine)palladium(0) or tetrakis(tri(o-tolyl)phosphine)palladium(0).

21. The process according to claim 13, wherein the hexaalkyl distannane is hexabutyl distannane.

* * * * *